(12) United States Patent
Wang et al.

(10) Patent No.: US 9,221,825 B2
(45) Date of Patent: Dec. 29, 2015

(54) PYRAZOLOPYRIMIDINONE COMPOUND AND IMIDAZO TRIAZONE COMPOUND FOR TREATING ERECTILE DYSFUNCTION

(75) Inventors: Jianping Wang, Yiwu (CN); Jianguo Wang, Yiwu (CN)

(73) Assignee: Zhejiang Dade Pharmaceutical Group Co., Ltd., Zhejiang (CN)

( * ) Notice: Subject to any disclaimer, the term of this patent is extended or adjusted under 35 U.S.C. 154(b) by 192 days.

(21) Appl. No.: 13/980,736

(22) PCT Filed: Jan. 20, 2012

(86) PCT No.: PCT/CN2012/070636
§ 371 (c)(1),
(2), (4) Date: Sep. 25, 2013

(87) PCT Pub. No.: WO2012/097750
PCT Pub. Date: Jul. 26, 2012

(65) Prior Publication Data
US 2014/0018351 A1  Jan. 16, 2014

(30) Foreign Application Priority Data
Jan. 21, 2011  (CN) .......................... 2011 1 0023784

(51) Int. Cl.
*A61K 31/551*  (2006.01)
*C07D 487/04*  (2006.01)
*A61K 9/20*  (2006.01)

(52) U.S. Cl.
CPC ............ *C07D 487/04* (2013.01); *A61K 9/2018* (2013.01)

(58) Field of Classification Search
CPC ........................... A61K 31/551; C07D 487/04
USPC ......................................... 514/218; 540/575
See application file for complete search history.

(56) References Cited

FOREIGN PATENT DOCUMENTS

| | | |
|---|---|---|
| CN | 1278822 A | 1/2001 |
| CN | 200410066281.7 | 3/2006 |
| CN | 102134242 A | 7/2011 |
| EP | 0 995 750 A1 | 4/2000 |
| EP | 1 199 070 A2 | 4/2002 |
| JP | 2000-128883 | 5/2000 |
| JP | 2002-528456 | 9/2002 |
| WO | 0147929 A1 | 7/2001 |
| WO | 99/24433 | 5/2009 |
| WO | WO 2011/154798 A1 | 12/2011 |

OTHER PUBLICATIONS

EPO Extended Examination Search Report for 12736699.5 dated May 16, 2014.

*Primary Examiner* — Brenda Coleman
(74) *Attorney, Agent, or Firm* — Greenberg Traurig, LLP; Fang Xie

(57) ABSTRACT

Disclosed are selective phosphodiesterase inhibitor compounds shown in formula (I) or (II) for treating Erectile Dysfunction, the pharmaceutically acceptable salts and configurational isomers thereof. In the formula, the substituents $R^1$, $R^2$, $R^3$, $R^4$ and $R^5$ are defined as in the specification. Also disclosed are methods for preparing same, and a medical composition comprising compounds of formula (I) or (II), and the use of these compounds for preparing a drug treating or preventing male Erectile Dysfunction.

3 Claims, No Drawings

PYRAZOLOPYRIMIDINONE COMPOUND AND IMIDAZO TRIAZONE COMPOUND FOR TREATING ERECTILE DYSFUNCTION

RELATED APPLICATIONS

This application is a national phase filing under 35 U.S.C. 371 of International Application No. PCT/CN2012/070636 filed on Jan. 20, 2012, which claims the benefit of and priority to Chinese Patent Application No. 201110023784.6 filed Jan. 21, 2011, both of which applications are hereby incorporated by reference in their entirety.

FIELD OF THE INVENTION

The present invention relates to the technical field of pharmaceutics, and specifically relates to a new kind of fast, long-term compounds for preventing or treating Erectile Dysfunction.

BACKGROUND ARTS

Erectile Dysfunction (ED) is a kind of diseases characterized by the inability to develop an erection of the penis, the inability to get the erection stronger, or the inability to maintain an erection, which may lead to the failure of a sexual performance. There are many causes of Erectile Dysfunction. The first cause which can lead to Erectile Dysfunction is a psychological cause such as the bad relationship between the couples, or the mental stress caused by some reasons. The second cause is a physiological cause such as the disorder of the erection center. The severe diseases, especially the long-term diseases of some important organs such as liver, kidney, heart, lung may also influence the mental control of sexual physiology. The incidence rate of Erectile Dysfunction will increase along with the increase of age. According to the survey in normal population in USA, the incidence rate was 8% in adult men, whereas the incidence rate was approximately 10% in China.

Nowadays, there are many kinds of methods for treating Erectile Dysfunction, among which the oral administration of drugs is most acceptable. Commercial drugs for oral administration for treating Erectile Dysfunction are mainly Sildenafil (Trade name: Viagra), Tadalafil (Trade name: Cialis), Vaedenafil (Trade name: Levitra).

Sildenafil, Tadalafil and Vaedenafil are all selective inhibitors of cyclic guanosine monophosphate (cGMP)-specific phosphodiesterase-5 (PDE5). The physiological mechanism of an erection of penis relates to the release of nitric oxide (NO) in the corpus cavernosum of penis during a sexual stimulus. NO activate guanylate cyclase, and then leads to the enhancement of cyclic guanosine monophosphate (cGMP) level, the relaxation of the smooth muscles in corpus cavernosum, and the sufficiency of blood. The tissue concentration of cGMP can be regulated with phosphodiesterase, and the most abundant phosphodiesterase in corpus cavernosum is the cGMP-specific phosphodiesterase-5 (PDE-5). Drugs such as Sildenafil enhance the effect of nitric oxide by inhibiting phosphodiesterase type 5 (PDE5), which decompose cGMP in corpus cavernosum. When a local NO release has been raised by a sexual stimulus, drugs such as Sildenafil can inhibit PDE-5, enhance cGMP level in corpus cavernosum, relax the smooth muscles, force blood to flow into corpus cavernosum, and then initiate an erection.

It has been proved by clinical researches in many countries around the world that Sildenafil is effective to Erectile Dysfunction caused by many kinds of reasons, and thus is a safe, effective, convenient drug for treating ED. However, drugs such as Sildenafil have some clinical side effects such as headache, rubeosis, dyspepsia, nasal obstruction and paropsia, and may even cause cardiovascular diseases such as the decline of supine blood pressure and the decline of cardiac output. Moreover, it is indicated by clinical researches that when a sexual performance is carried out after the administration of Sildenafil, the incidence rate of a cardiac disorder including symptoms such as angina pectoris, dizziness, nausea, etc. will increase, and may lead to cardiogenic sudden death.

Nowadays, as reported in EP0463756, CN1358722A, CN1283624A, etc., there are many methods for synthesizing Sildenafil in the world, which can be divided into two types:

(1) Firstly, an intermediate 1-methyl-2-phenyl-3-n-propyl-1,6-dihydro-7H-pyrazolo[4,3-d]pyrimidine-7-one is synthesized, then a sulfonyl chloride group is introduced into the benzene ring by the reaction with chlorosulfuric acid, and finally, it is linked with N-methylpiperazine and form a salt with citric acid.

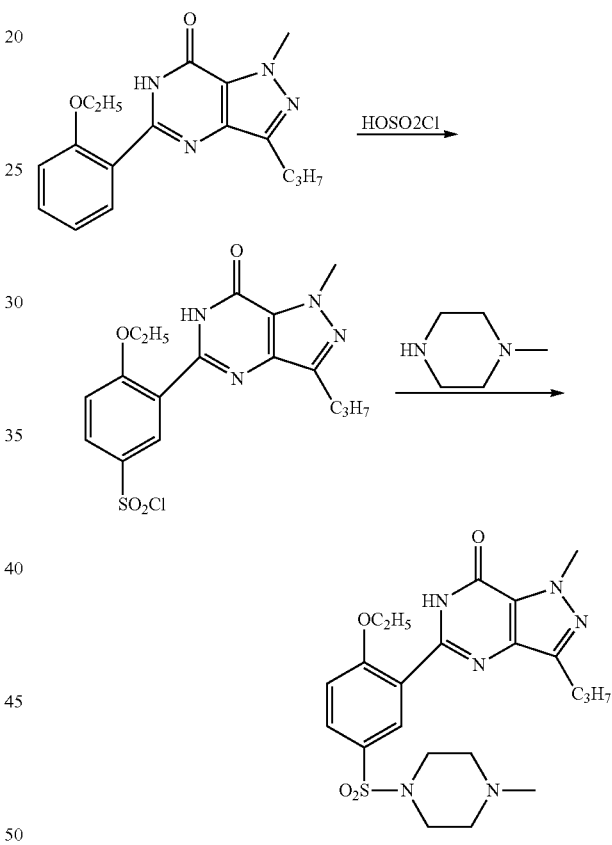

(2) An reaction between 1-methyl-3-propyl-4-aminopyrazole-5-carboxamide and 2-ethoxy-5-(4-methylpiperazine-1-sulfonyl)-benzoyl chloride is performed, and then Sildenafil is obtained by ring closure.

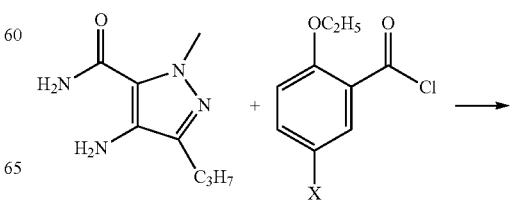

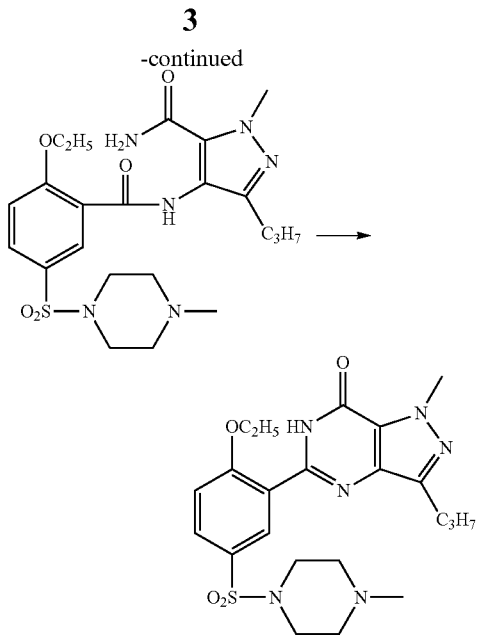

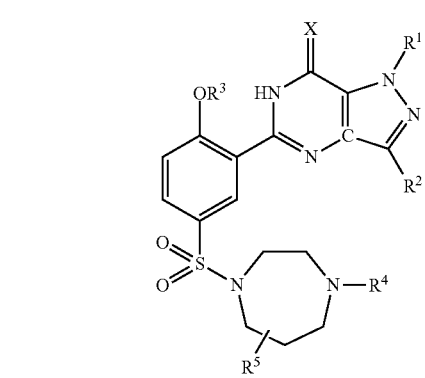

Further, we have found that when using a new compound obtained by using N-methylhomopiperazine instead of N-methylpiperazine during the synthesis of Sildenafil to perform animal experiments, the effective drug duration of the new compound is highly improved in comparison with Sildenafil under the same administration dosage during the treatment of Erectile Dysfunction, and the onset time thereof becomes short, and the toxicity and side effects thereof is declined.

Therefore, the present invention will disclose a 2-phenylpyrazolopyrimidone derivative for treating male Erectile Dysfunction.

SUMMARY OF THE INVENTION

Disclosed in the present invention are selective inhibitors of phosphodiesterase-5 (PDE5). In comparison with Sildenafil or Vaedenafil, the merit thereof lies in that the onset time is short and the effective drug duration is long.

The use of compound (I) and compound (II) or the pharmaceutically acceptable salts thereof or a medical composition comprising these compounds for treating or preventing male Erectile Dysfunction.

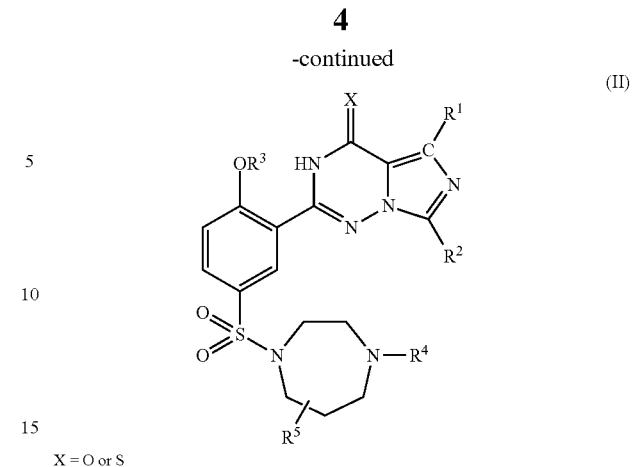

Wherein $R^1$, $R^2$ represent H, halogen, a $C_1$-$C_6$ alkyl which may be substituted by $C_1$-$C_3$ alkoxyl at any position, a $C_2$-$C_6$ alkenyl which may be substituted by $C_1$-$C_3$ alkoxyl at any position, a $C_1$-$C_6$ perfluoroalkyl or a $C_3$-$C_6$ cycloalkyl;

$R^3$ represents a $C_1$-$C_6$ alkyl which may be substituted by $C_1$-$C_3$ alkoxyl, a $C_2$-$C_6$ alkenyl which may be substituted by $C_1$-$C_3$ alkoxyl, a $C_1$-$C_6$ perfluoroalkyl, a $C_3$-$C_6$ cycloalkyl or a $C_3$-$C_5$ alkynyl;

$R^4$ represents H, a $C_1$-$C_6$ alkyl, a $C_2$-$C_6$ alkenyl, a $C_2$-$C_6$ alkynyl, a $C_3$-$C_6$ cycloalkyl; a $C_1$-$C_6$ alkyl, a $C_2$-$C_6$ alkenyl, a $C_2$-$C_6$ alkynyl, a $C_3$-$C_6$ cycloalkyl which may be substituted by hydroxyl, amino, cyan, carboxylic acid and its derivatives, sulfoacid and its derivatives;

$R^5$ represents one or several of identical or different substituents such as H, halogen, hydroxy, amino, cyan, carboxylic acid and its derivatives, sulfoacid and its derivatives, carbonyl, acyl, a $C_1$-$C_6$ alkyl, a $C_2$-$C_6$ alkenyl, a $C_2$-$C_6$ alkynyl, a $C_3$-$C_6$ cycloalkyl.

Compounds of formula (I) and (II) may form a salt with acids or acid substances such as citric acid, oxalic acid, hydrochloric acid, sulfuric acid, phosphoric acid, maleic acid, fumaric acid, tartaric acid, malic acid, succinic acid, methanesulfonic acid, p-toluenesulfonic acid, etc.

Wherein compounds of formula (I) are selected from

5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one, 5-[2-ethoxy-5-(3,4,5-trimethyl-1-homopiperazinylsulfonyl)]-phenyl-1-methyl-3-n-propyl-1,6-dihydro-7H-pyrazolo[4,3-d]pyrimidine-7-one, 5-[2-ethoxy-5-(3-acetylamino-4-methyl-1-homopiperazinylsulfonyl)]-phenyl-1-methyl-3-n-propyl-1,6-dihydro-7H-pyrazolo[4,3-d]pyrimidine-7-one, 5-[2-ethoxy-5-(4-methyl-5-hydroxy-1-homopiperazinylsulfonyl)]-phenyl-1-methyl-3-n-propyl-1,6-dihydro-7H-pyrazolo[4,3-d]pyrimidine-7-one, 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-thione, 5-[2-ethoxy-5-(3,4,5-trimethyl-1-homopiperazinylsulfonyl)]-phenyl-1-methyl-3-n-propyl-1,6-dihydro-7H-pyrazolo[4,3-d]pyrimidine-7-thione, 5-[2-ethoxy-5-(3-acetylamino-4-methyl-1-homopiperazinylsulfonyl)]-phenyl-1-methyl-3-n-propyl-1,6-dihydro-7H-pyrazolo[4,3-d]pyrimidine-7-thione, or 5-[2-ethoxy-5-(4-methyl-5-hydroxy-1-homopiperazinylsulfonyl)]-phenyl-1-methyl-3-n-propyl-1,6-dihydro-7H-pyrazolo[4,3-d]pyrimidine-7-thione.

Wherein compounds of formula (II) are selected from

2-[2-ethoxy-5-(4-methyl-1-homopiperazinylsulfonyl)]-phenyl-5-methyl-7-n-propyl-3H-imidazolo[5,1-f][1,2,4]triazine-4-one, 2-[2-ethoxy-5-(3,4,5-trimethyl-1-homopiperazinylsulfonyl)]-phenyl-5-methyl-7-n-propyl-3H-imidazolo[5,1-f][1,2,4]triazine-4-one, 2-[2-ethoxy-5-(4-methyl-5-hydroxy-1-homopiperazinylsulfonyl)]-phenyl-5-methyl-7-n-propyl-3H-imidazolo[5,1-f][1,2,4]triazine-4-one, 2-[2-ethoxy-5-(3-acetylamino-4-methyl-1-homopiperazinylsulfonyl)]-phenyl-5-methyl-7-n-propyl-3H-imidazolo[5,1-f][1,2,4]triazine-4-one, 2-[2-ethoxy-5-(4-methyl-1-homopiperazinylsulfonyl)]-phenyl-5-methyl-7-n-propyl-3H-imidazolo[5,1-f][1,2,4]triazine-4-thione, 2-[2-ethoxy-5-(3,4,5-trimethyl-1-homopiperazinylsulfonyl)]-phenyl-5-methyl-7-n-propyl-3H-imidazolo[5,1-f][1,2,4]triazine-4-thione, 2-[2-ethoxy-5-(4-methyl-5-hydroxy-1-homopiperazinylsulfonyl)]-phenyl-5-methyl-7-n-propyl-3H-imidazolo[5,1-f][1,2,4]triazine-4-thione, or 2-[2-ethoxy-5-(3-acetylamino-4-methyl-1-homopiperazinylsulfonyl)]-phenyl-5-methyl-7-n-propyl-3H-imidazolo[5,1-f][1,2,4]triazine-4-thione.

In the synthesis of compounds of formula (I), a prior drug intermediate 5-(2-ethoxy)-phenyl-1-methyl-3-n-propyl-1,6-dihydro-7H-pyrazolo[4,3-d]pyrimidine-7-one is used to prepare the corresponding sulfonyl chloride by sulfonation reaction. The specific scheme thereof is as below.

5-(2-ethoxy)-phenyl-1-methyl-3-n-propyl-1,6-dihydro-7H-pyrazolo[4,3-d]pyrimidine-7-one is reacted with chlorosulfuric acid, the obtained product is further linked with N-methylhomopiperazine, a white crystal is separated out, filtered, dried, and then the product is obtained.

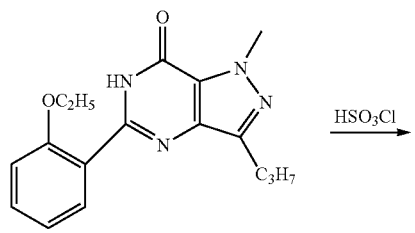

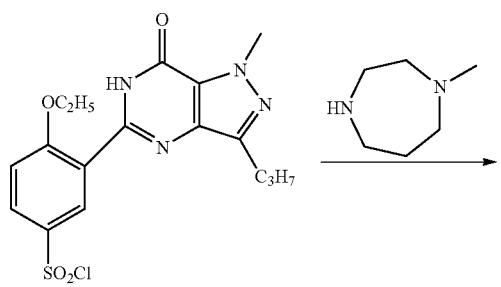

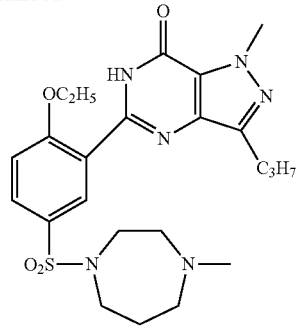

Further, 2-phenylpyrazolopyrimidone compounds can also synthesized by the following method.

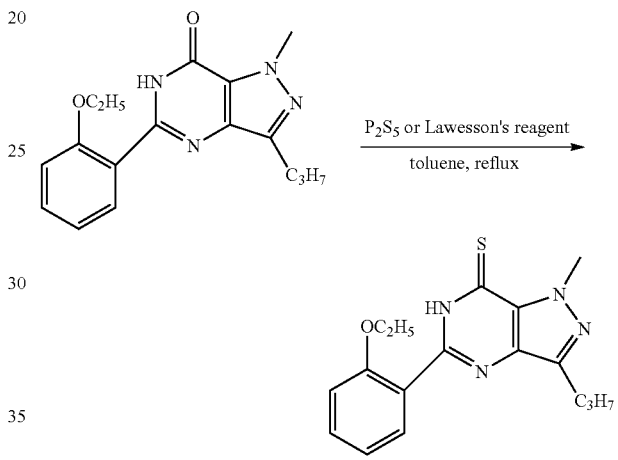

Compounds of formula (II) are obtained from the raw material 2-(2-ethoxy)-phenyl-5-methyl-7-n-propyl-3H-imidazolo[5,1-f][1,2,4]triazine-4-one by sulfonation reaction and the follow-up reaction with N-methylhomopiperazine. The raw material 2-(2-ethoxy)-phenyl-5-methyl-7-n-propyl-3H-imidazolo[5,1-f][1,2,4]triazine-4-one used in the reactions can be prepared in accordance with WO0250076.

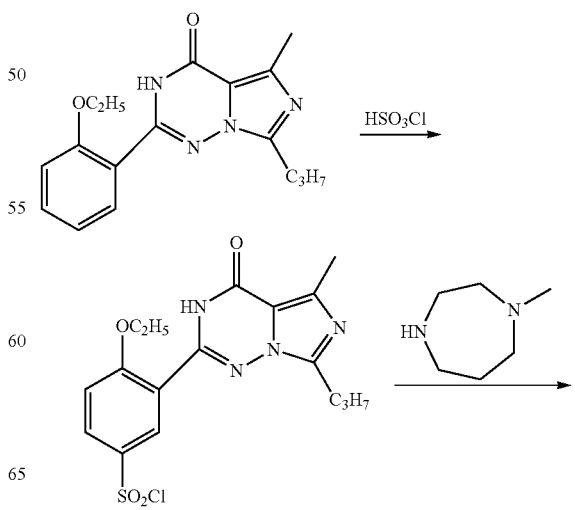

-continued

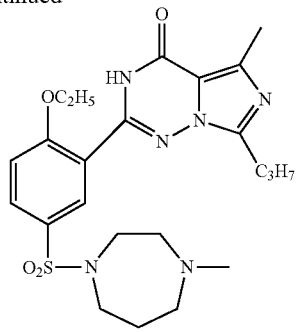

Further, the transformation between 2-(2-ethoxy)-phenyl-5-methyl-7-n-propyl-3H-imidazolo[5,1-f][1,2,4]triazine-4-one and thione can be carried out by the following method.

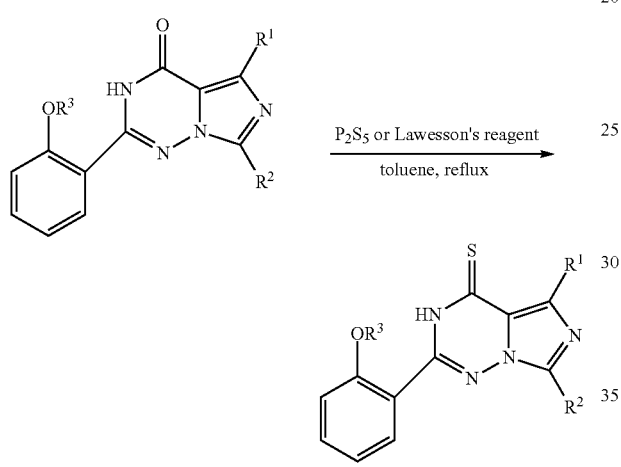

Further provided is a medical tablet comprising compound (I) and the production method thereof, wherein the tablet may contain several pharmaceutically acceptable vehicles including pharmaceutically general diluting agent, binder, disintegrating agent, lubricant.

Wherein the diluting agent includes starch, powdered sugar, dextrin, lactose, pregelatinized starch, microcrystalline cellulose, inorganic salts, mannitol; the binder includes distilled water, ethanol, starch slurry, carboxymethyl cellulose sodium, hydroxypropyl cellulose, methyl cellulose and ethyl cellulose, hydroxypropyl methyl cellulose, gelatin solution, sucrose solution and polyvinyl pyrrolidone solution; disintegrating agent includes dry starch, carboxymethyl starch sodium, low substituted hydroxypropyl cellulose, crosslinked polyvinyl pyrrolidone, crosslinked carboxymethyl cellulose sodium; lubricant includes magnesium stearate, aerosil, pulvistalci, hydrogenated vegetable oil, polyethylene glycol and magnesium dodecyl sulfate.

5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one citrate (ED9001), which is the preferred compound in the present invention, has been found that in the efficacy test in adult sexual mature male Sprague-Dawley rats, ED9001 has shown a distinct effect on improving catching times in comparison with the solution control group ($P<0.05$), and has shown a certain dose-effect relation. This suggests that it possesses a potential effect on enhancing sexual appetite and sexual performance. Further, the onset time is shorter and the effective drug duration is longer.

DETAILED DESCRIPTION OF THE INVENTION

Example 1

Preparation of 5-(2-ethoxy-5-chlorosulfonyl)-phenyl-1-methyl-3-n-propyl-1,6-dihydro-7H-pyrazolo[4,3-d]pyrimidine-7-one

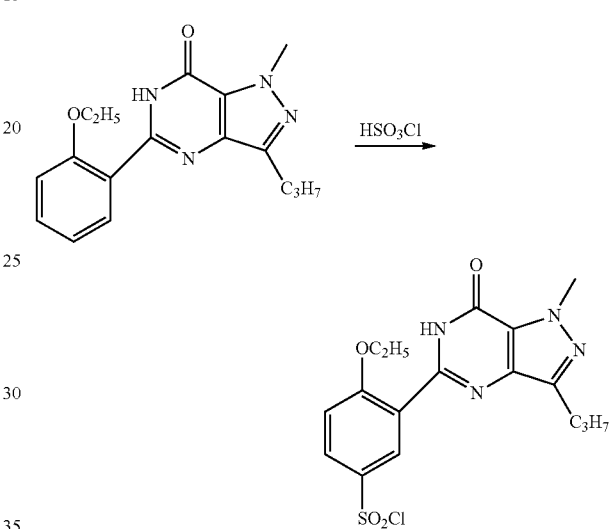

Chlorosulfuric acid (50 ml) was added into a 100 ml three-neck flask with a stirrer, 5-(2-ethoxy)-phenyl-1-methyl-3-n-propyl-1,6-dihydro-7H-pyrazolo[4,3-d]pyrimidine-7-one (31.2 g (0.1 mol)) was added in batches under stirring in an ice bath. The reaction was exothermic and was performed for 12 hrs. The reaction solution was slowly poured into icy water (100 g), a white solid was separated out, filtered, dried. A white solid (30 g) was obtained with a yield of 76%.

Example 2

Preparation of 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one

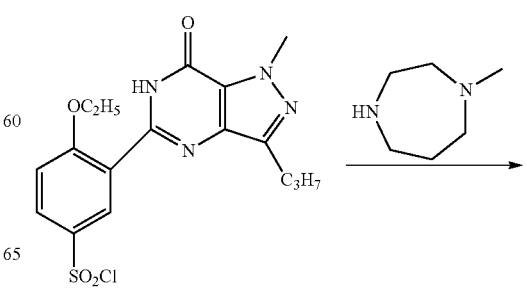

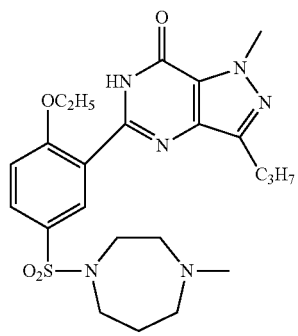

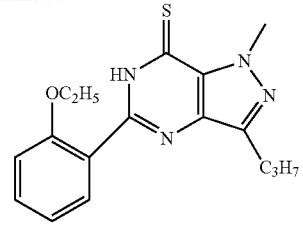

5-(2-ethoxy-5-chlorosulfonyl)-phenyl-1-methyl-3-n-propyl-1,6-dihydro-7H-pyrazolo[4,3-d]pyrimidine-7-one (20.5 g (0.05 mol)), dried chloroform (205 ml) were added into a 500 ml three-neck flask with a stirrer, stirred in an ice bath, and N-methylhomopiperazine (5.65 g) was further added, pH value was regulated to approximate 9 with diisopropyl ethylamine, and the reaction was performed for 12 hours. It was concentrated, ethyl acetate (200 ml) was added, washed with water, dried, and then a white solid (22.5 g) was obtained with a yield of 92.2%.

2-(2-ethoxy)-phenyl-1-methyl-3-n-propyl-1,6-dihydro-7H-pyrazolo[4,3-d]pyrimidine-7-one (50 g (0.16 mol)), phosphorus pentasulfide (17.8 g (0.08 mol)), pyridine (250 ml) were added into a 500 ml three-neck flask with a mechanical stirrer, stirred, heated and refluxed for 6 hours, TLC tracing was performed until the reactants were totally disappeared. The solvent pyridine was removed by distilling under reduced pressure, concentrated ammonia water ((25-28%) 75 ml) and ethanol 300 ml were added, heated and refluxed for 30 min. It was cooled, filtered, dried, and crude product (45 g) was obtained. The crude product was heated and solved into chloroform (150 ml), activated carbon (5 g) was added, stirring and reflux was performed for 30 min, it was filtered and the filtrate was washed with saturated brine and water consequently and dried with magnesium sulfate anhydrous, chloroform was removed by distilling, the obtained solid was re-crystallized with ethanol and dried, solid (38 g) was obtained with a yield of 72%.

Example 3

Preparation of 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one citrate 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one (4.88 g (0.01 mol)), acetone (50 ml) were added into a 100 ml three-neck flask with a stirrer, stirred in an ice bath, citric acid (1.92 g) was added, the reaction was performed for 12 hours, a white crystal was separated out, suction filtrated, dried, and then a white solid (6.23 g) was obtained with a yield of 90.5%.

Example 4

Preparation of 2-(2-ethoxy)-phenyl-1-methyl-3-n-propyl-1,6-dihydro-7H-pyrazolo[4,3-d]pyrimidine-7-thione

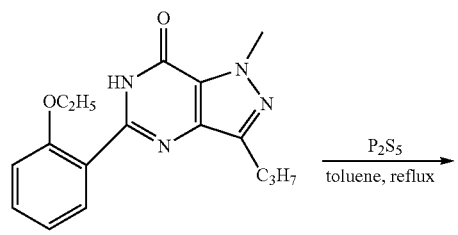

Example 5

Preparation of 2-(2-ethoxy-5-chlorosulfonyl)-phenyl-5-methyl-7-n-propyl-3H-imidazolo[5,1-f][1,2,4]triazine-4-one Chlorosulfuric acid (50 ml) was added into a 100 ml three-neck flask with a stirrer, 2-(2-ethoxy)-phenyl-5-methyl-7-n-propyl-3H-imidazolo[5,1-f][1,2,4]triazine-4-one (31.2 g (0.1 mol)) was added in batches under stirring in an ice bath. The reaction was exothermic and was performed for 12 hrs. The reaction solution was slowly poured into icy water (100 g), a white solid was separated out, filtered, dried. A white solid (30 g) was obtained with a yield of 76%.

Example 6

Preparation of 2-[2-ethoxy-5-(4-methyl-1-homopiperazinylsulfonyl)]-phenyl-5-methyl-7-n-propyl-3H-imidazolo[5,1-f][1,2,4]triazine-4-one

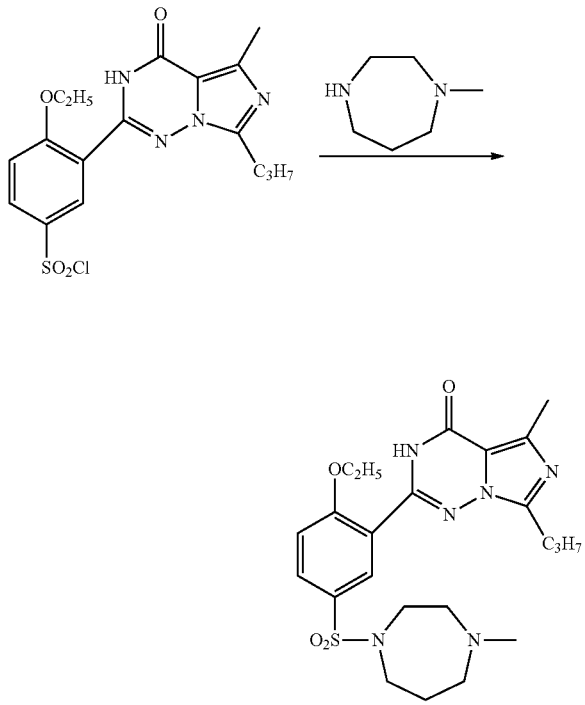

2-(2-ethoxy-5-chlorosulfonyl)-phenyl-5-methyl-7-n-propyl-3H-imidazolo[5,1-f][1,2,4]triazine-4-one (20.5 g (0.05 mol)), dried chloroform (205 ml) were added into a 500 ml three-neck flask with a stirrer, stirred in an ice bath, and N-methylhomopiperazine (5.65 g) was further added, pH value was regulated to approximate 9 with diisopropyl ethylamine, and the reaction was performed for 12 hours. It was concentrated, ethyl acetate (200 ml) was added, washed with water, dried, and then a white solid (22.5 g) was obtained with a yield of 92.2%.

Example 7

Preparation of 2-[2-ethoxy-5-(4-methyl-1-homopiperazinylsulfonyl)]-phenyl-5-methyl-7-n-propyl-3H-imidazolo[5,1-f][1,2,4]triazine-4-one citrate 5-[2-ethoxy-5-(4-methyl-1-homopiperazinylsulfonyl)]-phenyl-5-methyl-7-n-propyl-3H-imidazolo[5,1-f][1,2,4]triazine-4-one (4.88 g (0.01 mol)), acetone (50 ml) were added into a 100 ml three-neck flask with a stirrer, stirred in an ice bath, citric acid (1.92 g) was added, the reaction was performed for 12 hours, a white crystal was separated out, suction filtrated, dried, and then a white solid (6.23 g) was obtained with a yield of 90.5%.

Example 8

Preparation of 2-(2-ethoxy)-phenyl-5-methyl-7-n-propyl-3H-imidazolo[5,1-f][1,2,4]triazine-4-thione

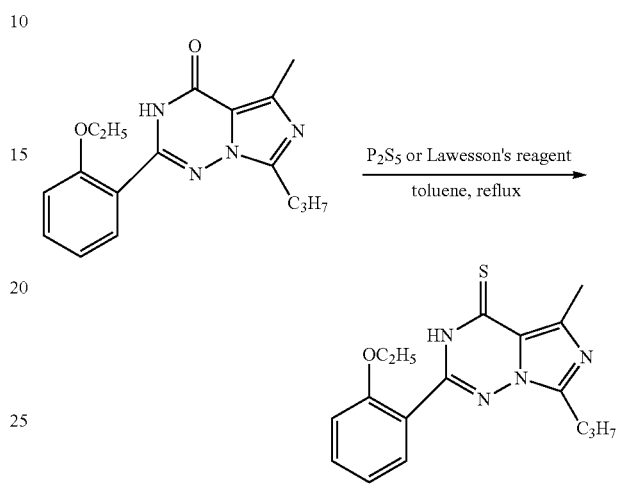

2-(2-ethoxy)-phenyl-5-methyl-7-n-propyl-3H-imidazolo[5,1-f][1,2,4]triazine-4-one (50 g (0.16 mol)), phosphorus pentasulfide (17.8 g (0.08 mol)), pyridine (250 ml) were added into a 500 ml three-neck flask with a mechanical stirrer, stirred, heated and refluxed for 6 hours, TLC tracing was performed until the reactants were totally disappeared. The solvent pyridine was removed by distilling under reduced pressure, concentrated ammonia water ((25-28%) 75 ml) and ethanol (300 ml) were added, heated and refluxed for 30 min. It was cooled, filtered, dried, and crude product (45 g) was obtained. The crude product was heated and solved into chloroform (150 ml), activated carbon (5 g) was added, stirring and reflux was performed for 30 min, it was filtered and the filtrate was washed with saturated brine and water consequently and dried with magnesium sulfate anhydrous, chloroform was removed by distilling, the obtained solid was re-crystallized with ethanol and dried, solid (38 g) was obtained with a yield of 72%.

Example 9

Preparation of Tablets

Prescription

| Name of raw material (adjuvant) | Dosage (unit: gram) |
| --- | --- |
| ED9001 | 50 |
| microcrystalline cellulose | 80 |
| lactose | 155 |
| pregelatinized starch | 20 |
| magnesium stearate | 4 |
| hydroxypropyl cellulose | 70 |
| crosslinked carboxymethyl cellulose sodium | 1 |
| calcium sulfate dihydrate | 20 |
| total | 400 |

The weight of the raw materials and all of the adjuvents were totally 400 g, they were crashed, sieved and then well mixed, granulated, pressed to 1000 tablets, 50 mg each.

Example 10

The Efficacy Test of the Drug for Anti-Erectile Dysfunction 80 adult sexual mature female clean grade Sprague-Dawley rats, whose body weight were 200±12 g and whose age were 8 weeks old, were selected for the test. Bilateral oophorectomy was performed under anesthesia by the intraperitoneal injection of 10% chloral hydrate, and penicillin (20000 U/kg) was intramuscular injected after the operation for 3 days. The test was performed 2 weeks after the oophorectomy, wherein estradiol benzoate (200 μg/kg) was intramuscular injected 48 hours before the test, and progesterone (2 mg/kg) was intramuscular injected 4 hours before the test so as to synchronize the oestrus for copulation test.

130 adult sexual mature male clean grade Sprague-Dawley rats, whose body weight were 200±13 g and whose age were 8 weeks old, were selected and stabilized for 2 weeks for use.

They were random divided into solvent control group (0.5% carboxymethyl cellulose sodium), positive control group (Sildenafil), drug for test group with high/medium/low dosage of ED9001, 20 rats in each group. The methods of administration, group division and the condition of administration were as following:

Administration route: intragastric administration;
Volume of administration: 1 mg/100 g bw
Solvent control group: 0.5% CMC-Na solution;
Sildenafil group: drug concentration 0.44 mg/ml;
ED9001 high dosage group: drug concentration 0.88 mg/ml;
medium dosage group: drug concentration 0.44 mg/ml;
low dosage group: drug concentration 0.22 mg/ml.

Observation was performed at 7:00-10:00 p.m., and the light in the room was dimmed with a red lamp for the observation. When the test began, the male rats were firstly put into cages and then observed for 10-20 min, the results were shown below in Table 1:

TABLE 1

The results of the efficacy test of ED9001 for anti-ED

| Group of drug | Number of rats | Dosage (mg/kg bw) | Latent period of catch behavior (s) | Catching times (times) | Riding times (times) |
| --- | --- | --- | --- | --- | --- |
| Solvent control group | 16 | — | 13.1 ± 4.7 | 24 ± 7 | 18 ± 7 |
| Sildenafil group | 15 | 4.4 | 12.5 ± 6.5 | 27 ± 6 | 24 ± 7 |
| ED9001 low dosage group | 12 | 2.2 | 12.1 ± 3.6 | 31 ± 9 | 24 ± 7 |
| ED9001 medium dosage group | 11 | 4.4 | 14.4 ± 7.5 | 26 ± 9 | 21 ± 7 |
| ED9001 high dosage group | 14 | 8.8 | 14.2 ± 4.9 | 32 ± 9 | 27 ± 10 |

According to the results, ED9001 has shown a distinct effect on improving catching times in comparison with the solution control group under half of the Sildenafil dosage ($P < 0.05$), and has shown a certain dose-effect relation. This suggests that it possesses a potential effect on enhancing sexual appetite and sexual performance.

Described above are only preferred examples of the present invention, not intended to limit the scope of the present invention. The substantial technical content of the present invention is generally defined within the scope as claimed in the claims. Any technical solutions or methods accomplished by any others will be regarded as falling within the scope of the claims, if they are the same as defined by the scope of the claims of the application or equivalent changes.

The invention claimed is:

1. A method for treating male Erectile Dysfunction, comprising administering an effective amount of 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one citrate to a patient in need thereof.

2. 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one citrate.

3. A pharmaceutical composition comprising 5-[2-ethoxy-5-(4-methyl-1-homopiperazinylsulfonyl)]-phenyl-1-methyl-3-n-propyl-1,6-dihydro-7H-pyrazolo[4,3-d]pyrimidine-7-one citrate and a pharmaceutically acceptable diluting agent or vehicle.

* * * * *